US00PP11400P

United States Patent [19]

Schuurman

[11] Patent Number: Plant 11,400

[45] Date of Patent: Jun. 6, 2000

[54] HYBRID TEA ROSE PLANT NAMED 'SUNTICK'

[75] Inventor: Frank Schuurman, Aukland, New Zealand

[73] Assignee: DeVor Nurseries, Inc., Watsonville, Calif.

[21] Appl. No.: 08/859,583

[22] Filed: May 20, 1997

[51] Int. Cl.[7] ..... A01H 5/00

[52] U.S. Cl. ..... Plt./137

[58] Field of Search ..... Plt./18, 19, 12, Plt./137, 138, 130

[56] References Cited

U.S. PATENT DOCUMENTS

P.P. 5,177 1/1984 Christensen ..... Plt./15

OTHER PUBLICATIONS

UPOV–ROM, 1998/01, Plant Variety Database, GTI Jouve Retrieval Software, citation for 'Suntick'.

Haring, ed., 1986, "Modern Roses 9", The American Rose Society, Shreveport, Louisiana, p. 114.

*Primary Examiner*—Howard J. Locker

*Attorney, Agent, or Firm*—Christie, Parker & Hale, LLP

[57] ABSTRACT

A hybrid tea rose variety producing pink flowers.

1 Drawing Sheet

BACKGROUND OF THE INVENTION

The present invention relates to a new and distinct hybrid tea rose variety which was originated by my crossing as seed parent the variety known as 'Jacaranda' and as pollen parent the variety known as 'Gold Medal (U.S. Plant Pat. No. 5,177).' The varietal denomination of this new rose is 'Suntick.'

SUMMARY OF THE INVENTION

Among the novel characteristics possessed by the new variety which distinguish it from its parents and all other varieties of which I am aware are its attractive, pink flowers borne on a bushy, vigorous plant.

Asexual reproduction by budding of the new variety as performed in Watsonville, Calif., shows that the foregoing and other distinguishing characteristics come true to form and are established and transmitted through succeeding propagations. Other known forms of asexual reproduction for roses may be also employed.

COMPARISON WITH PARENTS

Whereas 'Jacaranda' produces purple pink flowers and 'Gold Medal' is a yellow flowered grandiflora, the new variety produces pink flowers.

BRIEF DESCRIPTION OF ILLUSTRATION

The accompanying illustration show typical specimens of the vegetative growth and flowers of the new variety in different stages of development and depicted in color as nearly true as it is reasonably possible to make the same in a color illustration of this character.

BRIEF DESCRIPTION OF THE NEW VARIETY

Parentage: Seedling.

*Seed parent.*—'Jacaranda'.

*Pollen parent.*—'Gold medal'.

Class: Hybrid Tea.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Continuous.

A. Bud:

(1) *Size.*—Large.

(2) *Form.*—Pointed.

(3) *Color.*—Green bud near 145C.

(4) *Sepals.*—Long, some sepals foliaceous, sepals cover bud, then divide and fold back at maturity; about 3 to 4 cm in length. Color: Near 146B in center, near 144A at base.

(5) *Peduncle.*—Length: About 9 cm to about 12 cm. Aspect: Rough. Strength: Erect, sturdy. Color: Near 144A.

(6) *Bracts.*—None.

Bloom:

(1) *Size.*—Average size when fully expanded — about 12 cm to about 13 cm.

(2) *Borne.*—Singly.

(3) *Form.*—Imbricated, outer petals reflex to points, some petals curl under.

(4) *Petalage.*—Number of petals under normal conditions — about 36 to 42.

(5) *Color* (⅓–½ open).—Outer petals — Top Surfaces: Outer edge and tips: Near 58D Top part of Petal: Near 49D to 50D Bottom of petal near 4D Undersurface: Outer Edge: Near 62C Top part of Petal: Near 49D Bottom part of petal: Near 4D Inner petals — Top surface: Outer Edge: Near 62A Top part of Petal: Near 56B Bottom part of petal: Near 4D Undersurface: Edge: Near 62A Top part of Petal: Near 49D Bottom part of petal: Near 4D Base of petals: Near 4B General tonality from a distance: Pink (6) *Color* (*Fully open*).—Outer petals — Top surface: Edge: Near 62D Top part of Petal: Near 65D Bottom part of petal: Near 11D Undersurface: Edge: Near 62D Top part of Petal: Near 49D Bottom part of petal: Near 11D Inner petals — Top surface: Edge: Near 68D Top part of Petal: Near 62D Bottom part of Petal: Near 4D Undersurface: Edge of petal: Near 62D Top part of Petal: Near 155A Bottom part of petal: Near 157A Base of petals: Near 2D General tonality from a distance: Pink (7) *Color change.*—Petals fade to a lighter pink Petal top surface: Outer edge: Near 62D Rest of petal: Near 157A Petal undersurface: Outer edge: Near 62D Rest of petal: Near 157B Base of petals: Near 1D General tonality at a distance: Pink Petals:

(1) *Texture.*—Smooth, medium thick.

(2) *Appearance.*—Inside slightly matte and outside matte.

(3) *Form.*—Orbicular with edges reflexing and curling under.

(4) *Arrangement.*—Imbricated.

(5) *Petaloids.*—Many, about 9 to 10.

(6) *Persistence.*—Petals drop off cleanly.

(7) *Fragrance.*—Moderate old rose fragrance.

(8) *Lasting quality.*—On plant about 10 to 14 days; about 8 to 10 days after cutting.

REPRODUCTIVE ORGANS

A. Stamens:

(1) *Arrangement.*—Irregularly arranged around styles.

(2) *Stamens.—Anthers: Color — near* 21A. Filaments: Color — near 47B.

(3) *Pollen.*—Color — near 21A.

B. Pistils:

(1) *Styles.*—Bunched, irregular, uneven.

(2) *Stigmas.*—Color — near 20B.

C. Characteristics of hips: Not observed.

PLANT

A. Form: Upright, height about 107 to 122 cm and spread about 46 to 56 cm.

B. Growth: Vigorous.

C. Foliage: Compound 3 to 5 leaflets.

(1) *Size.*—Large.

(2) *Quantity.*—Abundant.

(3) *Color.*—New foliage — upper side near 147A underside near 147B with near 183A near edges; mature foliage — upper side near 147A, underside near 147B.

(4) *Shape.*—Oval.

(5) *Texture.*—Upper side leathery, semi-glossy; underside leathery, veiny.

(6) *Edge.*—Serrate.

(7) *Serration.*—Denticulate.

(8) *Leaf stem.*—Color — medium green.

(9) *Stipules.*—Long, adnate, curling downward.

(10) *Rachis.*—Small prickles underneath.

(11) *Petioles.*—Top near 147A with near 165A on edge, underside near 146C.

(12) *Auricle.*—Long, bearded margins.

(13) *Resistance to disease.*—Very resistant to mildew, rust and blackspot.

D. Wood:

(1) *New wood.*—Color near 146B with tinges of near 184B, bark smooth.

(2) *Old wood.*—Color near 144A, bark smooth.

E. Flower Stem: About 55 cm to about 67 cm from last cut.

F. Thorns:

(1) *Thorns.*—None, very few prickles.

G. Winter Hardiness: Winter hardy in Watsonville, Calif.

I claim:

1. A new and distinct hybrid tea rose plant of the variety substantially as shown and described.

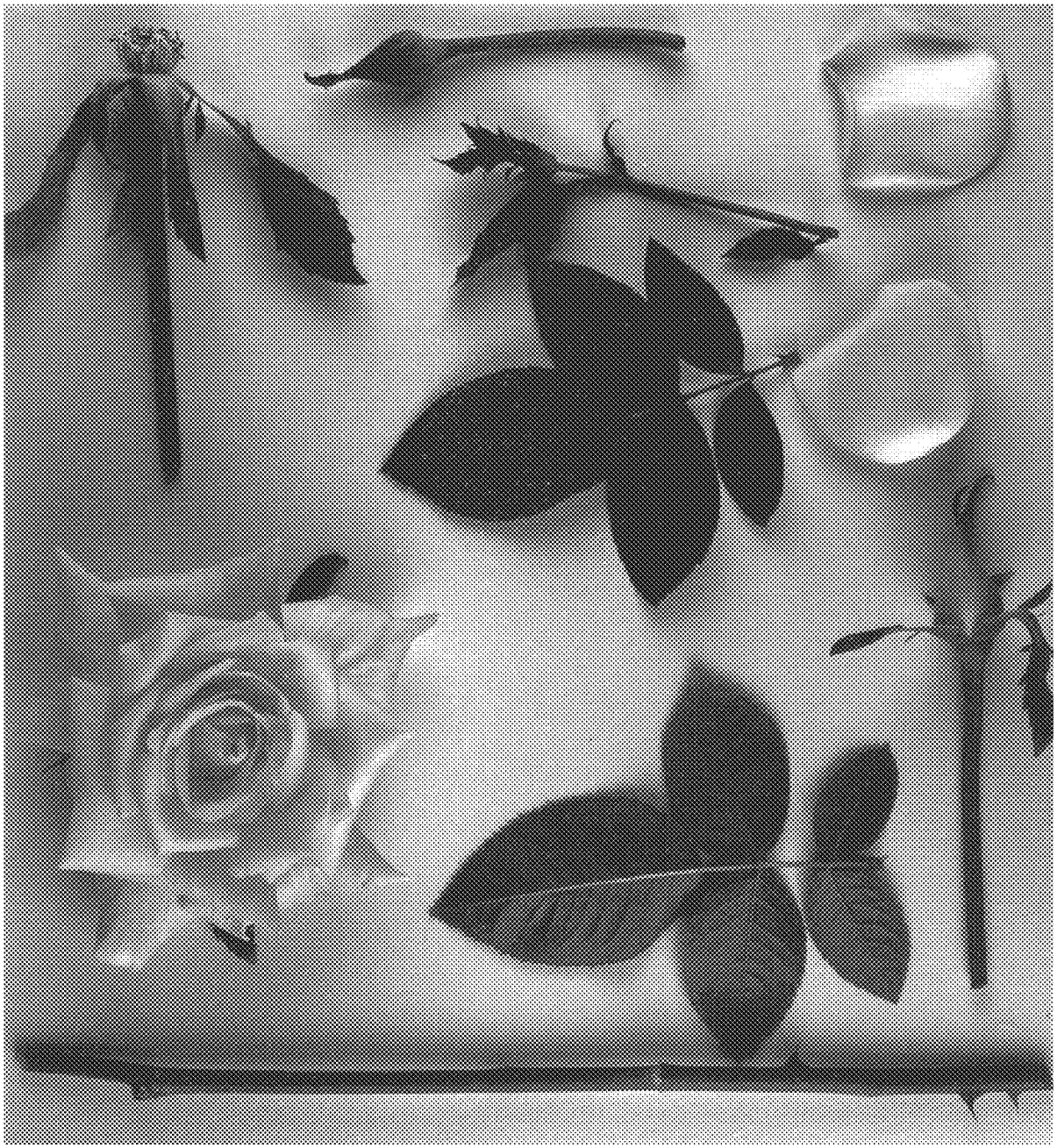

* * * * *